(12) United States Patent
House

(10) Patent No.: US 8,177,774 B2
(45) Date of Patent: May 15, 2012

(54) CATHETERIZATION ASSEMBLY

(75) Inventor: Jamie Glen House, Colorado Springs, CO (US)

(73) Assignee: Adapta Medical, Inc., Colorado Springs, CO (US)

( * ) Notice: Subject to any disclaimer, the term of this patent is extended or adjusted under 35 U.S.C. 154(b) by 162 days.

(21) Appl. No.: 11/505,315

(22) Filed: Aug. 17, 2006

(65) Prior Publication Data

US 2007/0088330 A1   Apr. 19, 2007

Related U.S. Application Data

(60) Provisional application No. 60/708,893, filed on Aug. 17, 2005.

(51) Int. Cl.
*A61M 27/00* (2006.01)

(52) U.S. Cl. .......................... 604/544; 604/172; 604/523

(58) Field of Classification Search ................... 604/171, 604/172, 265, 317, 327, 328, 540, 544, 523
See application file for complete search history.

(56) References Cited

U.S. PATENT DOCUMENTS

| | | | |
|---|---|---|---|
| 4,622,033 A | 11/1986 | Taniguchi | |
| 4,772,275 A | 9/1988 | Erlich | |
| 4,834,710 A | 5/1989 | Fleck | |
| 4,930,522 A * | 6/1990 | Busnel et al. | 128/844 |
| 5,149,326 A | 9/1992 | Woodgrift et al. | |
| 5,181,913 A | 1/1993 | Erlich | |
| 5,334,166 A | 8/1994 | Palestrant | |
| 5,779,670 A | 7/1998 | Bidwell et al. | |
| 5,792,114 A | 8/1998 | Fiore | |
| 5,827,247 A * | 10/1998 | Kay | 604/327 |
| 5,895,374 A | 4/1999 | Rodsten | |
| 6,053,905 A | 4/2000 | Daignault et al. | |
| 6,059,107 A | 5/2000 | Nosted et al. | |
| 6,090,075 A | 7/2000 | House | |
| 6,152,235 A * | 11/2000 | Woodruff | 168/5 |
| 6,176,849 B1 | 1/2001 | Yang et al. | |
| 6,217,569 B1 | 4/2001 | Fiore | |
| 6,409,717 B1 | 6/2002 | Israelsson et al. | |
| 6,471,684 B2 | 10/2002 | Dulak et al. | |
| 6,578,709 B1 | 6/2003 | Kavanagh et al. | |
| 6,602,244 B2 | 8/2003 | Kavanagh et al. | |
| 6,634,498 B2 | 10/2003 | Kayerod et al. | |
| 6,673,053 B2 | 1/2004 | Wang et al. | |
| 6,736,805 B2 | 5/2004 | Israelsson et al. | |
| 6,848,574 B1 | 2/2005 | Israelsson et al. | |
| 2001/0001443 A1 | 5/2001 | Kayerod et al. | |
| 2001/0007060 A1 | 7/2001 | Fiore | |
| 2001/0027295 A1 | 10/2001 | Dulak et al. | |
| 2001/0027299 A1 | 10/2001 | Yang et al. | |
| 2003/0018302 A1 | 1/2003 | Kavanagh et al. | |
| 2003/0083644 A1 * | 5/2003 | Avaltroni | 604/544 |
| 2003/0105423 A1 * | 6/2003 | Hughes | 604/27 |
| 2003/0130646 A1 * | 7/2003 | Kubalak et al. | 604/544 |

(Continued)

*Primary Examiner* — Tatyana Zalukaeva
*Assistant Examiner* — Benedict L Hanrahan
(74) *Attorney, Agent, or Firm* — Moazzam & Associates, LLC

(57) ABSTRACT

A disposable hydrophilic catheterization device for inserting a hydrophilic catheter into the urethra of an individual for the purpose of evacuating the bladder is disclosed. The catheter device includes a catheter introducer, a flexible hydrophilic catheter and a flexible thin-walled sheath. The sheath surrounds the urethra-insertable portion of the catheter, is adapted for containing a wetting liquid, and prevents pooling of the wetting liquid with collected urine. A leak-resistant diaphragm disposed within the catheter introducer is capable of being pierced by the catheter tip to form a leak-resistant orifice around the wetted hydrophilic catheter as it moves through the orifice.

18 Claims, 7 Drawing Sheets

U.S. PATENT DOCUMENTS

| | | |
|---|---|---|
| 2004/0074794 A1 | 4/2004 | Conway et al. |
| 2004/0153051 A1 | 8/2004 | Israelsson et al. |
| 2004/0163980 A1* | 8/2004 | Tanghoj et al. ............... 206/363 |
| 2004/0256264 A1 | 12/2004 | Israelsson et al. |
| 2005/0015076 A1 | 1/2005 | Giebmeyer et al. |
| 2005/0109648 A1 | 5/2005 | Kerzman et al. |
| 2005/0137582 A1 | 6/2005 | Kull-Osterlin et al. |
| 2005/0273052 A1* | 12/2005 | Jorgensen ..................... 604/103 |
| 2006/0025753 A1 | 2/2006 | Kubalak et al. |
| 2008/0097411 A1* | 4/2008 | House .......................... 604/544 |

* cited by examiner

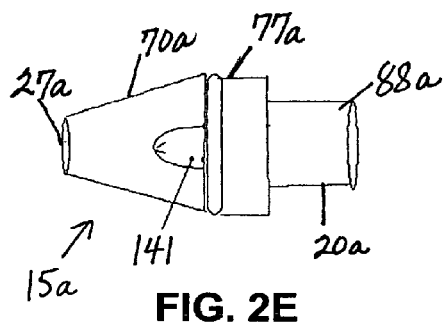
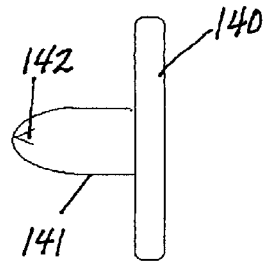
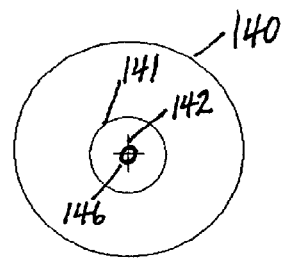
FIG. 2E  FIG. 5D  FIG. 5E
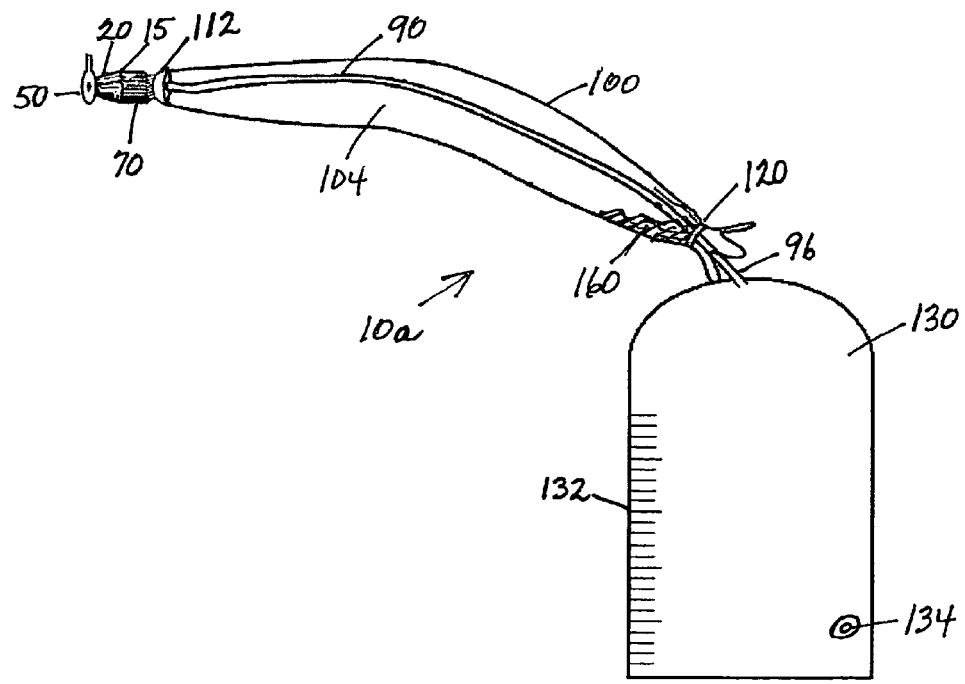
FIG. 8

FIG. 3A  FIG. 3B

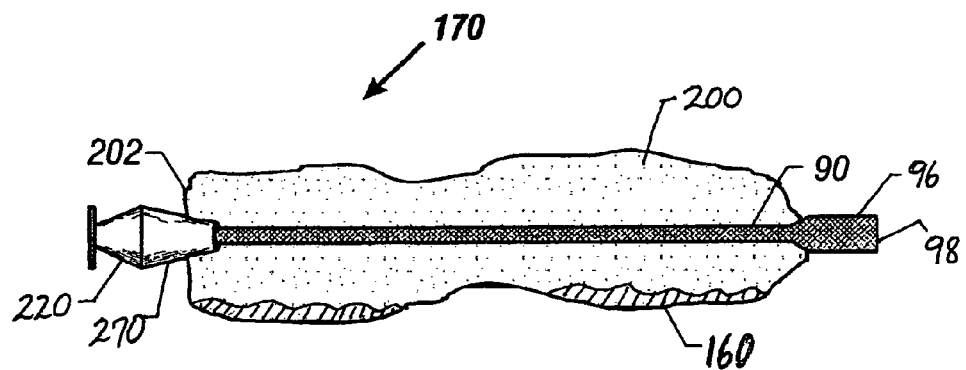
FIG. 6
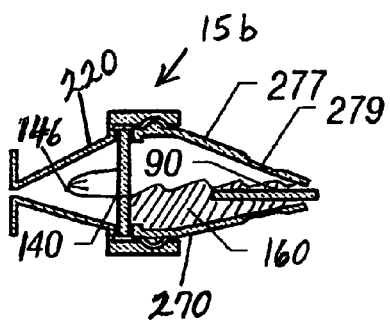 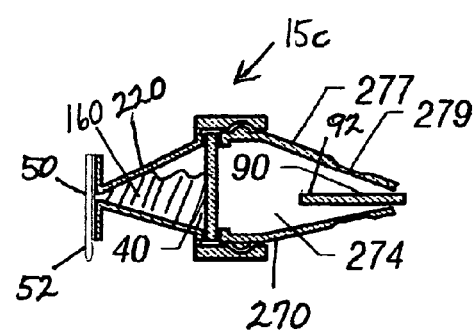
FIG. 7A FIG. 7B

CATHETERIZATION ASSEMBLY

This application claims priority to U.S. Provisional Patent Application Ser. No. 60/708,893, filed Aug. 17, 2005, the content of which is hereby incorporated by reference in its entirety into this disclosure.

BACKGROUND OF THE INVENTION

1. Field of the Invention

The present invention relates to catheter assemblies. More particularly, the present invention relates to catheter assemblies having multiple functions.

2. Background of the Invention

Short term, or repeated catheterization of an individual's urinary bladder is a common practice today for many persons who are in a hospital setting, a nursing home, doctor's office, rehabilitation facility or at home. For instance, a patient is sometimes catheterized to treat such conditions as urinary retention, the inability to evacuate urine, or for the purpose of obtaining a sterile urine specimen from a patient in a doctor's office.

The need for intermittent catheterization of an individual sometimes arises due to problems typically associated with long term use of indwelling catheters, such as infections, urethral damage, and bladder damage. Long term use of an indwelling catheter is also a risk factor for bladder cancer. This is often the case for persons having a neurogenic urinary condition, such as in a spinal cord injury, multiple sclerosis, stroke, trauma or other brain injury. Conditions that interfere with the individual's ability to voluntarily void the bladder may also arise post-surgically or as a result of benign prostatic hypertrophy or diabetes. Many of the affected individuals are capable of, and would prefer to perform self-catheterization. For many, the level of risk and discomfort of repeated catheterizations carried out over the course of a day (at 3-6 hour intervals, for example) are offset by the accompanying convenience, privacy or self-reliance that is achieved. Some of the major difficulties that arise in self-catheterization are the lack of satisfactory catheterization kits, the problem of maintaining the required level of sanitation during the procedure, and the difficulty of sometimes performing the procedure under conditions of restricted space and privacy.

In assisted, or non self-catheterizations, it is common practice in hospitals to employ a catheterization tray, which typically includes a sterile drape, gloves, a conventional catheter, antiseptic solution, swabs, lubricant, forceps, underpad and a urine collection container. Assisted catheterization is usually performed with the patient in a supine position. Maintaining a sterile field during the procedure can still be a problem, however, and the "cath tray" procedure is impractical for use with some individuals and situations today.

Many individuals with spinal cord injuries or other neurological diseases routinely perform intermittent catheterization several times a day using conventional catheters or kits and "clean technique." Clean technique means that the urethral area is initially swabbed with antiseptic, and efforts are made to avoid contamination of the catheter during the procedure. The user's hands are not sterile and a sterile field is not maintained. Clean technique is used instead of sterile technique, generally, for two reasons. First, it is very difficult, if not impossible, for individuals who are performing self-catheterization to adhere strictly to sterile technique. Secondly, these individuals are required to catheterize themselves between 3 and 6 times a day, and the cost of a new sterile catheter and the accessories required to perform sterile catheterization become excessively expensive for many users. Sometimes an individual will reuse a "cleaned" catheter. As a result, the use of non-sterile technique will many times result in contamination and subsequent infection of the urinary tract, causing significant morbidity and cost to the patient and society.

Even if cost considerations were not a major consideration for the user, with most conventional self-contained sterile units where the collection bag doubles as the catheter insertion cover, the catheter is extremely difficult for the user to grasp and insert. This is particularly a problem for self-catheterization users who may also have neurological problems that limit manual dexterity. Also, with some of the available catheter kits and methods, the catheter is either not sufficiently lubricated during insertion (and thus requires the additional application of possibly non-sterile lubricant), or the catheter is too slick with lubricant and cannot effectively be grasped through an insufficiently flexible bag. As a practical matter, most individuals who would prefer to self-catheterize cannot conveniently do so, and maintain the required level of sanitation using many of the existing catheterization apparatus.

A significant difficulty with conventional catheterization assemblies that merely package the catheter inside a sterile urine collection bag is that the flexible bag is typically neither thin-walled and pliant enough to permit grasping and feeding the catheter into the urethra, nor is it sufficiently rigid for accurate urine output measurement or for specimen removal. With some of the available catheter kits, there is also the further problem of a flexible or slippery catheter tending to drop down into the collection bag. In this circumstance, the user must first maneuver the catheter tip back to the bag opening before the catheter can be inserted into the patient's urethral opening.

Some catheterization devices in use today employ hydrophilic catheters that are self-lubricating when wetted with water prior to use. Furthermore, there are devices used for wetting a hydrophilic urinary catheter, which include a wetting receptacle that defines a wetting fluid receiving area for receiving the catheter and a wetting fluid container.

While the elimination of a dry catheter and lubricant may have some advantages, a serious drawback that is common to many hydrophilic catheter arrangements and catheterization methods is the tendency for the wetting liquid to flow out of the end of the catheter and onto the user or the user's bed or wheelchair as the catheter is drawn out of its packaging. Another drawback is that some hydrophilic catheter kits do not prevent the slippery hydrophilic catheter from falling down into an attached urine collection bag. As a consequence, the user must manipulate the catheter tip back to the bag opening before the catheter can be inserted into the patient's urethra. If the catheter slips into the urine collection bag after removal from the urethra, it can skew the urine collection volume. Still another problem with some conventional devices is that the wetting liquid can pool with the collected urine, skewing volume measurements and urinalysis results.

Accordingly, there remains a need for a better hydrophilic catheter assembly that avoids the above-mentioned problems. What is needed is an easy-to-use, disposable catheterization assembly that includes a hydrophilic catheter and is practical for use by health care providers and by individuals alike, and which is suitable for self-catheterization.

SUMMARY OF THE INVENTION

The present invention provides a new catheter device or assembly that permits essentially sterile catheterization of the bladder and establishment of free drainage of urine from the discharge end of the catheter without using conventional sterile field technique. The new catheter assembly is an alternative to, or an improvement over, existing "unitized" self-lubricating catheterization assemblies. In accordance with certain exemplary embodiments of the present invention, a urinary catheterization device is provided that generally includes a (a) catheter introducer including a first guide section including an inlet for receiving a urinary catheter tip and a second guide section including an aperture for releasing the catheter tip, the aperture adapted for contacting a urethral opening; (b) a catheter including a tip having at least one urine inlet, a urine outlet, and an outer surface, at least a urethra-insertable portion of the outer surface being hydrophilic, the catheter tip being initially disposed in the first guide section; (c) a flexible walled sheath comprising first and second ends, a lumen, and a length that is less than that of the catheter, the sheath first end being sealingly attached to the catheter at a non-urethra-insertable location on the catheter adjacent to the outlet, and the sheath second end being sealingly attached to the first guide section, whereby the catheter tip is retained in the first guide section and prevented from slipping into the sheath lumen, the inlet and at least the urethra-insertable portion of the catheter being enclosed in the sheath lumen, the sheath adapted for containing a liquid for wetting the hydrophilic catheter or at least the urethra-insertable portion thereof; (d) a diaphragm disposed in the catheter introducer between the first and second guide sections, and adapted for being pierced by the catheter tip and for deterring or preventing leakage of the wetting liquid from the first guide section into the second guide section before and after being pierced by the catheter tip.

In certain embodiments, the diaphragm includes an extension that protrudes into the second guide section and is substantially conformable to the shape of the catheter tip and to the circumference of a moving catheter. In certain embodiments, the first guide section includes a cavity in fluid flow communication with the sheath lumen, and the sheath lumen and/or the first guide section contains an amount of the wetting liquid sufficient to wet the hydrophilic outer surface of the catheter to render the catheter lubricious. In certain embodiments, the second guide section comprises a cavity adapted for initially containing at least an amount of the wetting liquid sufficient to wet the hydrophilic outer surface of the catheter to render the catheter lubricious, and wherein the diaphragm is capable of preventing flow of the wetting liquid into the first guide section prior to the diaphragm being opened. In some embodiments, the second guide section is resiliently compressible. In certain embodiments, the flexible walled sheath is impermeable to the wetting liquid and may also comprise a grip enhancing surface.

In certain embodiments, an above-described catheterization assembly also includes a urine collection bag attached to a non-urethra-insertable site on the catheter. The collection bag is adapted for receiving the catheter urine outlet.

Advantageously, the urine outlet is separated from the sheath lumen so that the sheath lumen is not in fluid communication with the collection bag, and thus the wetting liquid is prevented from entering the urine collection bag. In certain embodiments, the sheath first end is sealingly attached to the catheter adjacent to the site of attachment of the urine collection bag, or adjacent thereto.

In certain embodiments, the sheath is of approximately equal length to that of the urethra-insertable catheter portion and the catheter tip is retained in the first guide section and is prevented from slipping into the sheath interior when the device is fully extended.

In some embodiments, an above-described catheterization device includes a removable closure sealing the catheter outlet. In certain embodiments, catheterization device includes a body-contacting collar and a frustoconical segment having its smallest outer diameter adjoining the collar.

In certain embodiments, the first and second guide sections are releasably joined together such that the diaphragm is removable, and in other embodiments they are fixedly joined together with the diaphragm disposed therebetween. In certain embodiments of an above-described catheterization device the diaphragm includes a conformable fluid barrier.

Also provided in accordance with certain embodiments of the present invention is a kit for catheterizing a urinary bladder, including a catheterization device as described above, a disposable package enclosing the catheterization device; and at least one antiseptic swab. In certain embodiments, the kit includes an attachable urine collection vessel having volumetric indicia.

Further provided in accordance with certain embodiments of the present invention is a method of deterring or preventing spillage of a wetting liquid during catheterization of a urinary bladder. The method includes: (a) providing an above-described device including an attached urine collection vessel, or providing an above-described device without an attached urine collection vessel and providing for urine disposal or collection; (b) placing the catheter introducer outlet against the urethral opening of an individual in need of catheterization; (c) grasping the flexible walled sheath and wetted hydrophilic catheter together at one or more first position or series of positions along the urethra-insertable length of the catheter, and urging the catheter tip into the diaphragm such that the diaphragm is pierced and such that a portion of the sheath is caused to collapse toward the first guide section; (d) re-grasping the flexible walled sheath and wetted catheter together at one or more second position or series of positions along the urethra-insertable length of the catheter, and moving the catheter tip through the pierced diaphragm, whereby a further portion of the sheath is caused to collapse toward the first guide section and the pierced diaphragm or a portion thereof forms a leak resistant slidable seal around the moving catheter; (e) re-grasping the flexible walled sheath and wetted catheter together at one or more third position or series of positions along the urethra-insertable length of said catheter, and urging the catheter tip through said second guide section, through said outlet, into the urethra and into the urinary bladder, whereby a further portion of said sheath is caused to collapse toward said first guide and urine flows into said catheter tip and out said urine discharge outlet; (f) after emptying the bladder, removing the catheter from the bladder and urethra by substantially reversing each of steps (e)-(b). In certain embodiments, the method also includes (g) measuring the amount of urine collected in said container.

Still further provided in accordance with certain embodiments of the present invention is a method of deterring or preventing spillage of a wetting liquid during catheterization of a urinary bladder. This method includes: (a) providing an above-described catheterization device wherein the aperture of the catheter introducer, from which the catheter exits, initially has a removable seal, and the second guide section contains at least an amount of a wetting liquid sufficient to wet the hydrophilic outer surface of the catheter to render the catheter highly lubricated or slippery. The method further includes (b) providing for urine disposal or collection, if the device does not include an attached urine collection container. In accordance with this method, the flexible walled sheath and the catheter are grasped together at one or more first position or series of positions along the urethra-insertable length of the catheter, and by urging the catheter tip into the diaphragm, the diaphragm is pierced, and a portion of the sheath is caused to collapse or gather toward the first guide section. The method further includes (d) withdrawing the catheter tip from the pierced diaphragm leaving an opening between said first and second guide sections which allows said wetting liquid to enter said first guide section. If necessary, (e) at least a soft second guide section of the catheter introducer is squeezed or compressed with the fingers of the user, to facilitate movement of the wetting liquid through said diaphragm opening and into said first guide section and sheath interior. After the catheter inside the sheath and first guide section is wetted by the liquid, the procedure continues with removing the seal and placing said catheter introducer outlet against the urethral opening of an individual in need of catheterization. The seal or closure is sufficiently strong to resist leakage from aperture of the pressurized liquid when the second guide section is squeezed. The method further includes (g) returning said wetted catheter tip through said diaphragm opening forming a leakage resistant seal around the moving catheter; (h) regrasping said flexible walled sheath and wetted catheter together at one or more subsequent position or series of subsequent positions along the sheath-enclosed urethra-insertable length of said catheter, and urging the catheter tip through said second guide section, through said outlet, into the urethra and into the urinary bladder, whereby further portions of said sheath are caused to collapse toward said first guide, until urine flows into said catheter tip and out said urine discharge outlet; (i) after emptying the bladder, removing the catheter from the bladder and urethra by reversing step (h).

An above-described catheterization device according to the present invention is an economic and desirable alternative to conventional catheterization trays used by health care personnel. The present catheter device is simple to use for either assisted or self-catheterization, with the individual in either a supine or non-supine position. The hydrophilic catheterization device and its method of use provide a decreased risk of contamination and infection over other "unitized" assemblies, and provide for easy waste disposal or collection for measurement or analysis using a conventional container without skewing of such measurements due to pooling of the wetting liquid with the collected urine. This device and catheterization method is practical for use by health care providers in hospitals, mobile emergency facilities, doctors' offices, rehabilitation facilities, nursing homes and the like. It is also advantageous for performing temporary catheterizations by individuals, is easy to use for self-catheterization in the home or in a public restroom, and provides for a high degree of sanitation during handling and use. A catheterization kit according to the present invention also lends itself to being economically manufactured and sold for one-time-only use, which will be of great benefit in reducing the incidence of urethral and bladder infections in catheterization patients. These and other features and advantages will be apparent from the detailed description and drawings that follow.

BRIEF DESCRIPTION OF THE DRAWINGS

FIG. 2E is a side view, in cross-section, of another catheter introducer according to an exemplary embodiment of the present invention.

FIG. 3A is a perspective view showing the second guide section of a catheter introducer according to an exemplary embodiment of the present invention as may be employed in the exemplary embodiments shown in FIGS. 2A-B.

FIG. 3B shows the outlet end of the second guide section of FIG. 3A.

FIG. 5D is a side profile view of a leakage-blocking diaphragm according to an exemplary embodiment of the present invention as employed in the catheter introducer shown in FIG. 2E.

FIG. 5E is a top view of the diaphragm as shown in FIG. 5D.

FIG. 6 is a side view of a catheterization device in accordance with an exemplary embodiment of the present invention.

FIGS. 7A-C are enlarged cross sectional views of a catheter introducer according to certain exemplary embodiments of the present invention; FIG. 7A illustrates first guide section containing wetting liquid and a catheter tip; FIG. 7B illustrates a second guide section containing wetting liquid; FIG. 7C omits the second guide section and employs a removable diaphragm cover.

FIG. 8 is a side view of a catheterization device including a collection bag, in accordance with an exemplary embodiment of the present invention.

DETAILED DESCRIPTION OF THE INVENTION

Figure 1A:
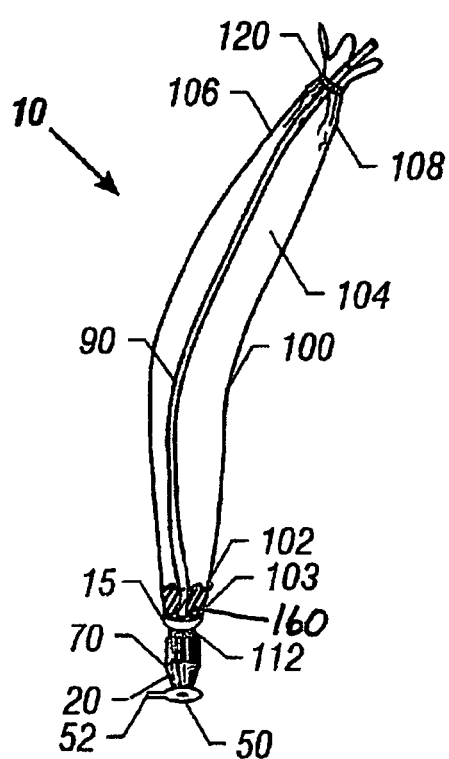
FIG. 1A is a side view of a urinary catheterization device according to an exemplary embodiment of the present invention.
Figure 9:
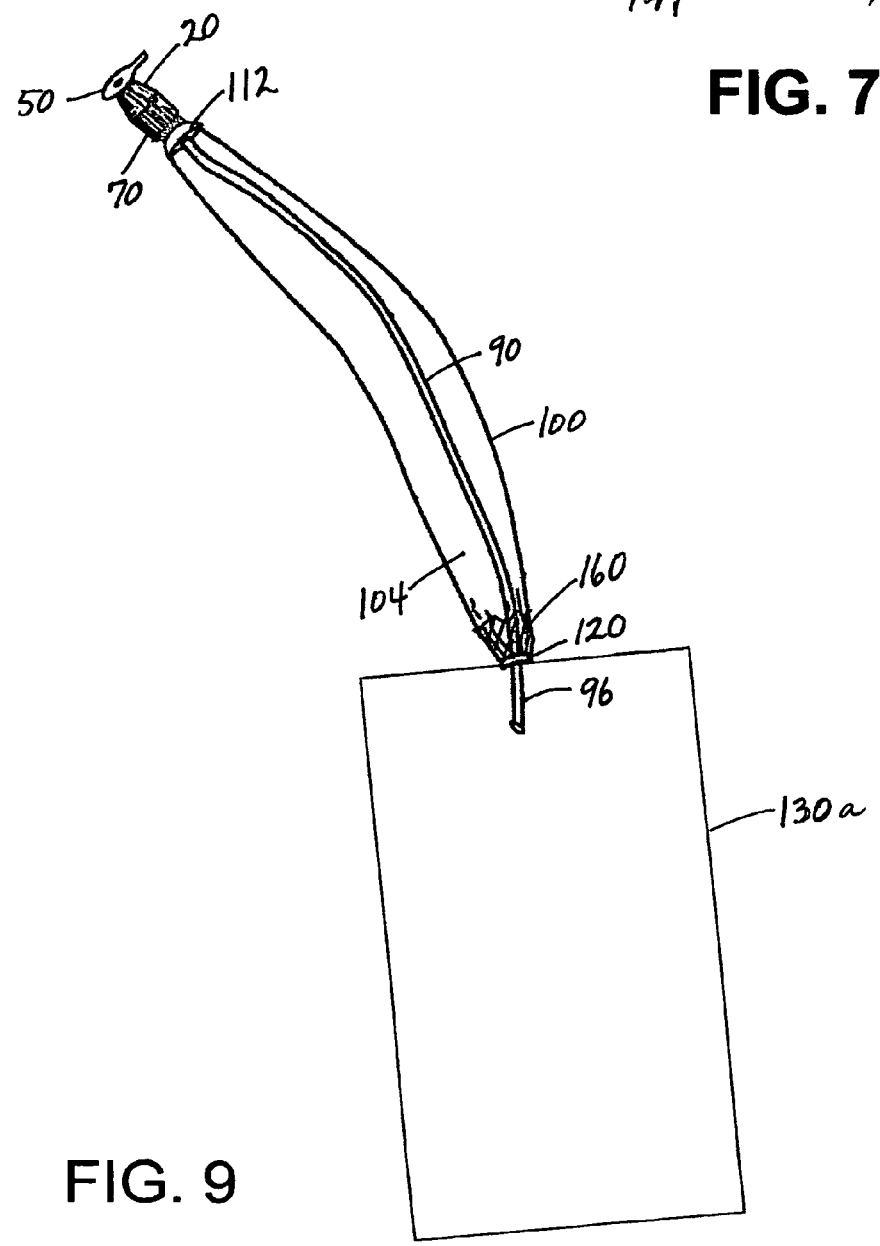
FIG. 9 is an elevation view of another catheterization device including a urine collection bag according to an exemplary embodiment of the present invention.

The present invention serves to address the shortcomings of conventional devices and assemblies on the market, and provide additional advantages and features not available to such conventional products. Referring to FIG. 1A, catheter device 10 includes a catheter introducer 15, a hydrophilic catheter 90, a thin-walled pliable sheath 100, and first and second sheath closures 112, 120. Optionally, a urine collection bag is pre-attached or can be attached by the user (FIGS. 8 and 9). Catheter 90 is preferably similar to, or the same as, a conventional hydrophilic urinary catheter, or it may be of any suitable hydrophilic urinary catheter design. All, or at least the portion of the catheter that is to be introduced into the urethra, is either coated with a hydrophilic material (e.g., PVC catheter coated with polyvinylpyrrolidone (PVP)), or is formed from a suitable hydrophilic material (e.g., silicone). In either case, the catheter is referred to as a "hydrophilic catheter" in this disclosure. As used herein and throughout this disclosure, the term "hydrophilic material" refers to a material that associates with water and becomes lubricious or slippery when wet. When wetted, the hydrophilic material that coats the catheter, or from which the catheter or a portion thereof is made, renders the catheter's outer surface slippery, reducing the frictional properties of the catheter when it slides over urethral tissues. The hydrophilic material is biocompatible or at least tolerated by the body for intermittent contact with urethral tissue. Preferably the hydrophilic substance does not dissolve readily in water, in order to promote long-term shelf life of a pre-wetted catheter in certain embodiments of the catheter device, such as those shown in FIGS. 1A, 2C and 6.

Figure 2A:
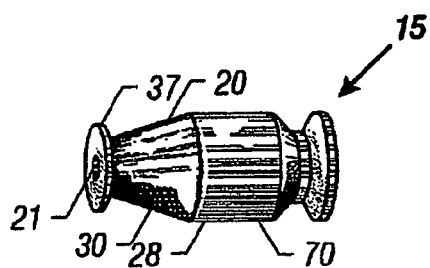
FIG. 2A is a side view of a catheter introducer according to an exemplary embodiment of the present invention.
Figure 2B:
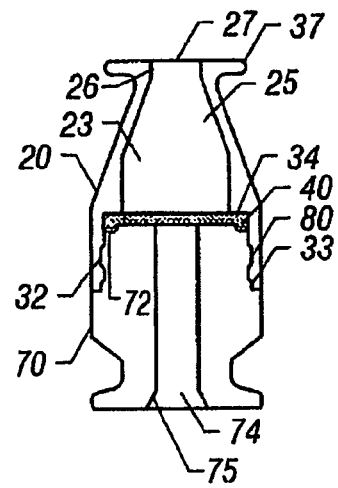
FIG. 2B is a side view, in cross section, of the catheter introducer of FIG. 2A.
Figure 2D:
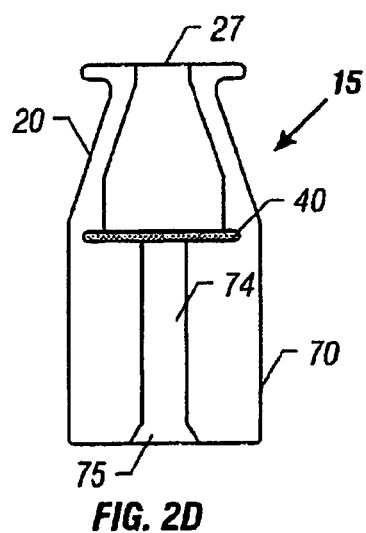
FIG. 2D is a side view, in cross-section, of a catheter introducer according to an exemplary embodiment of the present invention.
Figure 2C:
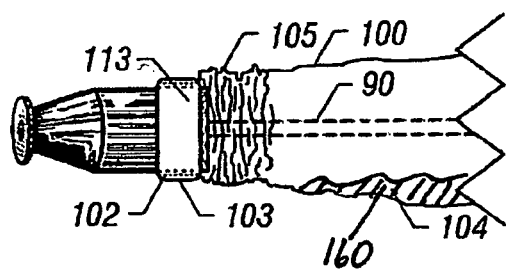
FIG. 2C is a side view of another embodiment of a catheterization device according to the present invention.

Catheter introducer 15, shown in FIGS. 2A-C includes first and second guide sections 70, 20, as separable pieces, or in the form of an integral, or monolithic structure with a fluid-blocking diaphragm 40 positioned between the first and second guide sections (as depicted in FIG. 2D). The monolithic configuration may be preferred in some instances for ease of manufacture and for cost considerations. First guide section 70 and second guide section 20 may be made of rigid, semi-rigid or soft (compressible) transparent or translucent plastic or silicon, but another suitable material may also be used as long as the resulting catheter introducer is biocompatible, sterilizable and also provides sufficient structural support to the catheter during use of the device. The outer surfaces of the catheter introducer may be smooth, or may have a roughened or textured outer surface to facilitate grasping by the user.

Figure 3C:
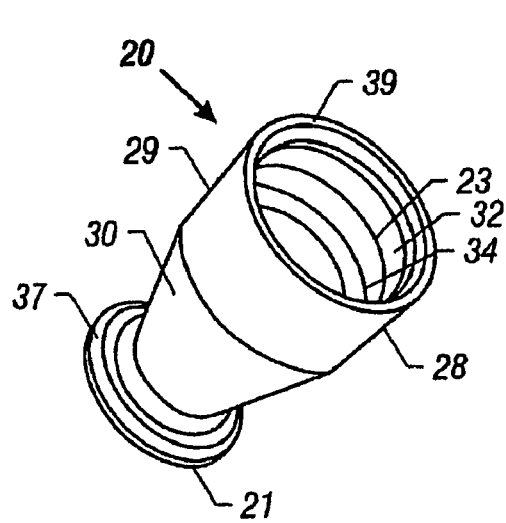
FIG. 3C is a side view, in cross-section, of the second guide section of the catheter introducer according to an exemplary embodiment of the present invention as may be employed in the embodiments shown in FIGS. 2A-B.
Figure 3C:
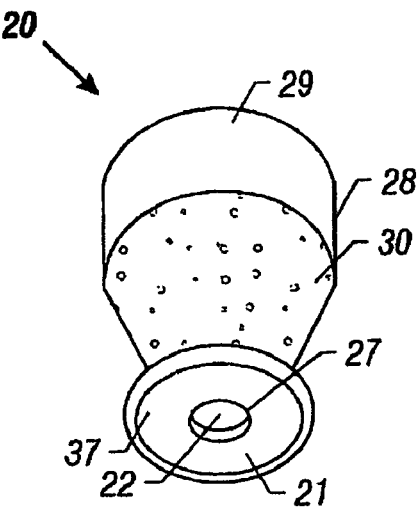
Figure 3C:
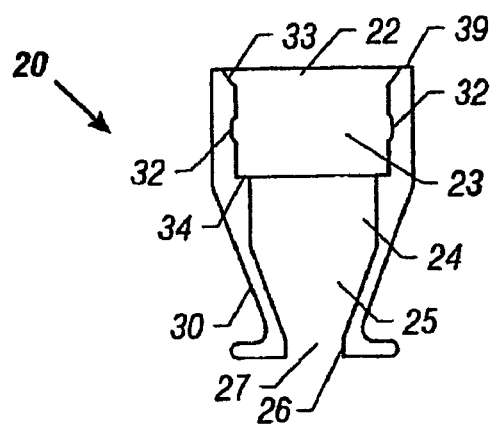

Referring to the embodiments shown in FIGS. 3A-C, second guide section 20 includes end 21, end 39, an outer surface 28 extending between ends 21, 39 and a central throughbore 22. Disposed at end 21 is a body contacting collar or flange 37. Outer surface 28 includes a generally cylindrical segment 29 adjacent end 39, and a frustoconical segment 30 that extends between cylindrical segment 29 and flange 37. Throughbore 22 includes a plurality of coaxially aligned bore segments, including receptacle portion 23 that is adjacent end 39, a reduced diameter portion 24, a tapered portion 25 and a neck portion 26 that is adjacent to end 21. An annular ledge or lip 34 is formed in throughbore 22 between receptacle portion 23 and reduced diameter portion 24. Receptacle portion 23 includes a beveled edge 33 at end 39 and an annular recess or groove 32 formed between lip 34 and beveled edge 33. If desired, cylindrical portion 29 and/or segment 30 may include a roughened or textured surface (as indicated in FIG. 3B), which may be created during casting of second guide section 20 or by scoring or machining of outer surface 28. Alternatively, throughbore 23 may have an essentially uniform diameter from end 21 to end 39 (similar in appearance to throughbore 74 shown in FIGS. 2B and 2D), for ease of manufacturing.

Figure 4A:
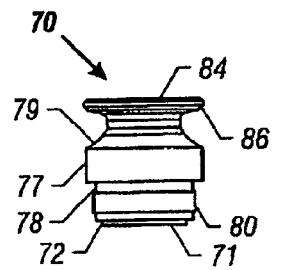
FIG. 4A is a side view of the first guide section according to an exemplary embodiment of the present invention as may be employed in the catheter introducer shown in FIGS. 2A-B.
Figure 4B:
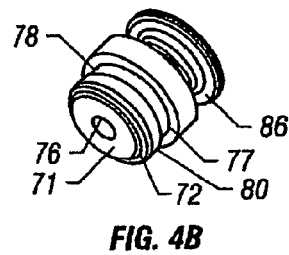
FIG. 4B is a perspective view of the first guide section of FIG. 4A.
Figure 4C:
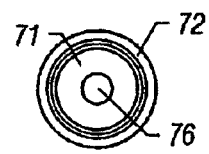
FIG. 4C is an end view of the first guide section of FIG. 4A showing the end that joins to the second guide section.
Figure 4D:
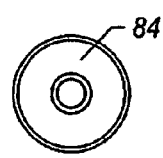
FIG. 4D is an end view of the first guide section of FIG. 4A showing the catheter inlet at the opposite end from that of FIG. 4C.
Figure 4E:
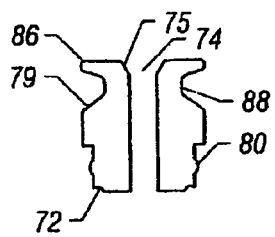
FIG. 4E is a cross sectional view of the first guide section shown in FIG. 4A.
Figure 4F:
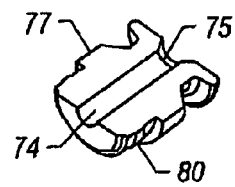
FIG. 4F is a perspective cross sectional view of the first guide section shown in FIG. 4B.

First guide section 70, as shown in FIGS. 4A-F, is a generally cylindrical member having a coupling portion 78, a sheath retaining portion 79 and a central portion 77 disposed therebetween. First guide section 70 further includes end 71, end 84, and a central throughbore 74. Throughbore 74 includes an outlet 76 adjacent to end 71, and a tapered inlet 75 adjacent end 84, as shown in FIGS. 4E-F. Sheath retaining portion 79 includes a sheath retaining collar 86 at end 84 and an annular recess or neck 88 between collar 86 and central portion 77. Coupling portion 78 is substantially cylindrical and may include an annular lip 72 at end 71 and an annular ridge or protrusion 80 disposed between lip 72 and central portion 77. As shown in FIG. 4B and described in more detail below, coupling portion 78 is sized so as to be matingly received within receptacle portion 23 of the second guide section 20 (FIG. 3A).

Similar catheter introducers 15a, 15b and 15c are illustrated in FIGS. 2E, 7A and 7B. Catheter introducer 15a (FIG. 2E) illustrates a device that is suitable for production as a unitary monolith, having simply a narrow throughbore 74a, elongated neck 88a, central portion 77a, and diaphragm 40 disposed between portion 25 of second guide section 20 and central portion 77a. The introducer 15b (FIG. 7A) has a modified throughbore which allows for larger interior cavities in guide sections 270 and 220. The first guide section is adapted for initially containing a wetting liquid. The catheter introducer 15c (FIG. 7B) is like that of FIG. 7A, but is adapted for initially holding a wetting liquid in the second guide section.

Figure 5A:
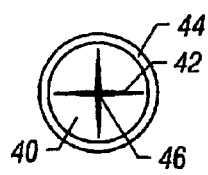
FIG. 5A is a top view of the diaphragm according to an exemplary embodiment of the present invention as shown in FIGS. 2B, 2D.
Figure 5B:
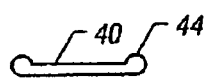
FIG. 5B is a side profile view of the diaphragm shown in FIG. 5A according to an exemplary embodiment of the present invention.
Figure 5C:
FIG. 5C is a side profile view of another diaphragm as employed in FIG. 5A according to an exemplary embodiment of the present invention.

Referring to FIGS. 2B, 2D and 7B, disposed between first and second guide sections 70, 20 is a fluid-blocking membrane or diaphragm 40. Preferably, diaphragm 40 is made of an elastomeric material (e.g., silicone or a like material) capable of sealing and retaining a wetting liquid on either side of the unpierced diaphragm, and is also able to withstand a conventional sterilization procedure. Diaphragm 40 (FIGS. 5A-C and 7B) preferably includes a central scored portion 42 to facilitate piercing by the tip end 92 of catheter 90 to form an aperture 46, but remains sufficiently sealed to retain the wetting liquid in the first guide section, until the catheter tip is pushed against the central region 42 of the diaphragm to force an opening or aperture 46 (FIG. 5A) in the scored area. In FIG. 2B, diaphragm 40 is disposed between annular lip 72 of guide member 70 and annular ledge 34 of reservoir member 20. As shown in FIGS. 2B and 5A-B, diaphragm 40 may be substantially flat and include a raised annular ring 44 that engages annular lip 72 of guide 70 and annular ledge 34 of reservoir 20 to help form a good seal. Alternatively, as shown in FIGS. 5C and 7B, the raised annular ring 44 is omitted from resilient diaphragm 40, and annular lip 72 of first guide section 70 is also omitted, for ease of manufacturing.

FIG. 2E, FIGS. 5D-E and FIG. 7A depict a another exemplary diaphragm for use in the catheterization device. This fluid blocking diaphragm 140 includes an extension 141 that is conformable to the shape and outer diameter of the catheter to help form and maintain a leak-resistant barrier to the wetting liquid as a wetted hydrophilic catheter moves through the scored area 142 to create aperture 146. The configuration of diaphragm 140 may otherwise be similar to that shown in FIG. 5B or 5C. Alternatively, any other suitable diaphragm design may be employed which is also capable of preventing flow of the water/saline out of the device along with the emerging catheter. This feature ensures that the wetting fluid will not spill out on the user or the user's bed, wheelchair, clothing and so forth. The fluid-blocking diaphragm maintains the wetting liquid in the area of the sheath and the first guide section of the catheter introducer.

Referring again to the catheter, as shown in FIGS. 1A-B and 7A-B, flexible hydrophilic catheter 90 of device 10 has a tip region or end 92 and an opposite region or end 96. Near tip end 92 is at least one urine inlet 94, and at the opposite end 96 is urine outlet 98. Initially, end 92 of catheter 90 is slidably and rotatably retained within first guide section 70, but not touching diaphragm 40. For example, the catheter tip rests in throughbore 74 of first guide section 70 and at a location between diaphragm 40 and tapered inlet 75 (FIGS. 2B and 2D). Similarly, catheter 90 is held in place in first guide section 70 by a thin-walled pliable sheath 200, as depicted in FIG. 6.

Alternatively, as shown in FIG. 7A-B, the catheter tip is disposed in first guide section 270 having a relatively larger bore or interior cavity than that shown in FIGS. 2B and 2D, for example. This configuration may be preferable when a hydrophilic catheter is sufficiently rigid to be directed into and pierce the diaphragm without need for supplemental support by a narrow throughbore.

Figure 1B:
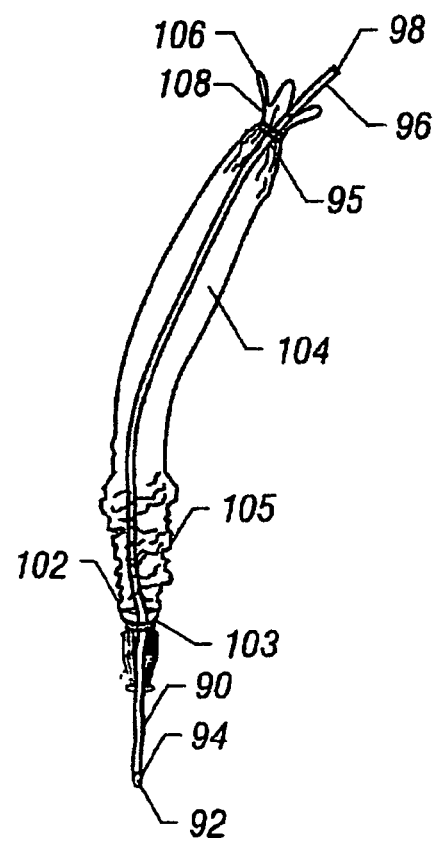
FIG. 1B shows the catheterization device of FIG. 1A with the catheter partially extended, as during insertion.

In FIGS. 1A-B, sheath 100 has an end 102, an opposite end 106, a lumen 104 and closure points 103, 108. Closure point 103 near end 102 is fixedly attached to first guide section 70 in annular recess 88, for example (FIG. 4E), and closure point 108 near end 106 is fixedly attached to catheter 90 at closure point 108 adjacent end 106 that coincides with sealing point 95, adjacent urine discharge outlet 98 of catheter 90, such that sheath 100 encloses catheter 90 from annular recess 88 of guide 70 to a point 95 along catheter 90 near end 96. Closures 120, 112 may be plastic or elastomeric ties or bands, or any other suitable closure means. The length of catheter that is covered by the sheath between the sheath closure points is at least the portion of the catheter that will be inserted into the urethra, plus the length that will remain inside the catheter introducer during a catheterization procedure, plus the length that is needed or desired to remain outside of the first guide section to accommodate the collapsed or gathered up sheathing, as illustrated in FIGS. 1B and 2C. The wetted hydrophilic catheter tends to be more difficult to grasp securely through the pliable sheath wall than a dry catheter, so the interior surface of the sheath may be modified or texturized so as to improve gripping. Preferably about 2-3 inches (5.1-7.6 cm) of the catheter extends beyond closure 120, is not hydrophilic and/or can remain dry so as to facilitate attachment of a urine collection vessel for ease of use.

In another representative configuration of catheter device 10 (shown in FIG. 2C), annular recess 88 of first guide section 70 is omitted, as are ties 112, 120, and sheath end 112 is instead held firmly in place by a compression ring 113. Other techniques of attaching the sheath to the catheter introducer could also be substituted, such as heat fusion, an adhesive or glue (FIG. 6), as long as contaminants are excluded by the closures during handling and use of the catheterization device, leakage of the wetting liquid is prevented, and the sheath lumen and the urine collection vessel are not in fluid communication. The embodiment of FIG. 2C or FIG. 6 may be preferred in some instances for ease of manufacture and for cost considerations.

The interior or lumen 104 of sheath 100 should be large enough to permit a catheter 90 to slide therein as the sheathing material collapses and is gathered up during use, yet not so large that the sheath is cumbersome. Using a conventional hydrophilic catheter the sheath diameter is preferably about 1.5 to 2.5 inches (3.8-6.4 cm) and about 2-3 inches shorter than the catheter. For example, catheters in typical use today range in diameter from about 8 French up to about 22 French, and are usually about 14 inches (35.6 cm) long.

In an exemplary embodiment of the present device, a sterile wetting liquid 160, such as water or saline is present inside the sheath lumen and/or inside the throughbore or cavity of the first guide section, and the liquid is able to move freely between those two areas as the orientation of the device varies (FIGS. 2C, 6, 7A, 8 and 9). As a result, the catheter can be maintained in pre-wetted condition, ready to use without separately applying a lubricant. The sterilized catheterization device may be stored until needed for use, while the pre-wetted catheter retains its lubricious property.

Instead of or in addition to placing the wetting liquid inside the sheath, a suitable amount of wetting liquid 160 may be contained in second guide section 220, as illustrated in FIG. 7B. In this configuration, the liquid 160 is initially retained in the second guide section by an intact diaphragm 40 or 140 and by a removable closure such as sealing tape 50 (also shown in FIGS. 1A, 6 and 8) which may be adhesively attached to body contacting collar 37 of end 21 to cover at least aperture 27, and also retained by the diaphragm between the two guide sections. Optionally, a removable close-fitting cap or plug (not shown) may be substituted for tape 50 and tab 52 (FIG. 1A). The second guide section is preferably made of a resilient yet flexible material that will provide support for the catheter and provide a satisfactory interface between the catheter introducer 15 and the urethral opening of the body, and yet is also capable of being squeezed or compressed to expel the wetting liquid through an opening in the diaphragm and into the first guide and sheath area. In this case, the closure at end 21 is preferably strong enough to resist the force of the liquid when the second guide section is compressed. For ease of manufacturing, the first and second guide sections may be made of the same compressible material (e.g., silicone).

Figure 7C:
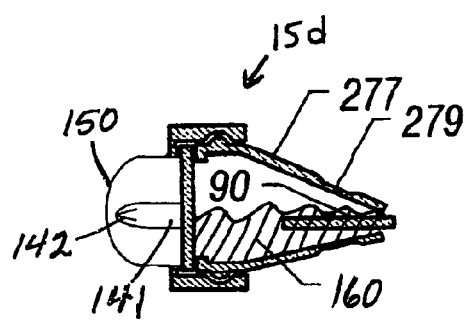

A similar configuration for a catheter introducer is shown in FIG. 7A in which first and second guide sections 270, 220 are made of the same or different material and are joined together or formed as a single unit locking diaphragm 240 in place between the two sections. The first guide section is capable of holding a sufficient amount of wetting liquid 160, such as water, saline or another suitable solution, and may be attached to the first end 202 of sheath 200, as illustrated in FIG. 6. First guide section 270, shown enlarged in FIGS. 7A-B, is tapered or substantially conical or frustoconical in shape to facilitate guidance of the catheter tip into the membrane and thence out of the second guide section, and to make it easier for the user to see how to position the catheter introducer. The second end 202 of sheath 200 can be attached to tapered region 277 at annular recess 279 on first guide section 270. The relatively large throughbore 274 (compared to that shown in FIG. 2D, for instance) provides adequate support for most hydrophilic catheters, and the larger cavity can accommodate a larger amount of liquid for wetting the surface of the hydrophilic catheter. Diaphragm 140 is preferably similar to diaphragm 40 and includes a leakage-deterring extension 141 that protrudes into second guide section 220. To further minimize the escape of wetting liquid from the device in the event that a small amount of the wetting liquid leaks from sheath/first guide through the diaphragm, a cap or cover may be provided at the body-contacting end of introducer 15, 15a, 15b or 15c. For example, the cover may be similar to the cover 50 with pull-tab 52, as illustrated in FIGS. 1A and 7B. Still another alternative configuration of the catheterization device employs an abbreviated introducer 15d, as shown in FIG. 7C, having no second guide section and employing a removable cover 150 over the diaphragm that is contoured to accommodate the shape of the diaphragm extension 141. This design also provides additional protection against leakage of the wetting liquid, as might occur, for example, if the scored region 142 were to become partially opened during handling of the device.

Referring primarily to FIG. 8, a catheterization device similar to that shown in FIG. 1A is advantageously combined with a urine collection bag 130. Catheterization device 10a includes a catheter introducer 15, sheath 100 containing a predetermined amount of wetting liquid 160, a hydrophilic catheter 90, and a urine collection bag 130. The collection bag is pre-attached, or is attachable, to the catheter so as to enclose end 96. Because the interior of first guide section 70 is open to the lumen of the sheath, the wetting liquid is also free to flow into first guide section 70 when the catheter device is shaken, tilted or the liquid is otherwise moved around in the sheath to ensure thorough wetting of the hydrophilic catheter prior to use. Alternatively, the wetting liquid 160 may be stored in the second guide section, as described above, for release into the first guide section and sheath at the time of use. Typically, the hydrophilic catheter will only require exposure to the liquid for about 20-30 seconds to become adequately lubricious. A configuration similar to that of FIG. 8 is shown in FIG. 9, in which the urine collection bag 130a is attached at the sheath closure site 120, for ease of manufacture. For example, the sheath closure and collection bag attachment may be accomplished by heat pressing or by attachment of a collar. The urine collection bag is not open to the sheath lumen 104. A feature of these and other embodiments of the catheterization device is that the closed sheath prevents the wetting liquid from pooling with the collected urine and from skewing output volume measurements and preventing dilution of urine analysis samples.

Referring again to FIGS. 2B, 3A-C, and 4A-F, catheter introducer 15 is assembled by disposing diaphragm 40 of catheter device 10 against lip 34 in throughbore 22 of second guide section 20. The coupling portion 78 of first guide section 70 is then inserted into receptacle portion 23 of second guide section 20 until annular ridge 80 is captured within annual recess 32 of second guide section 20. End 92 of catheter 90 is then inserted into tapered inlet 75 and throughbore 74 of guide 70, and is then further inserted until end 92 is adjacent to diaphragm 40. Care is taken so as not to prematurely pierce diaphragm 40 during assembly and prior to use. End 102 of sheath 100 is next disposed about annular recess 88 of guide 70 and fastened thereto by closure band 112. Similarly, band 120 attaches end 106 of sheath 100 to catheter 90 at closure point 108.

In another exemplary embodiment of catheter device 10 (shown in FIG. 2C), annular recess 88 of catheter guide 70 is omitted, as are ties 112, 120, and sheath end 112 is firmly attached by a compression ring 113. Other ways of attaching the sheath to the catheter introducer could also be substituted, such as heat fusion, an adhesive or glue (FIG. 6), as long as contaminants are sufficiently excluded by the closures during handling of the catheterization device, leakage of the wetting liquid is prevented, and the sheath lumen and the urine collection vessel are not in fluid communication. The embodiment of FIG. 2C or FIG. 6 may be preferred for ease of manufacture and for cost considerations.

An amount of wetting liquid, preferably water or saline, that is sufficient to thoroughly wet the catheter is placed in the sheath prior to sealing. Alternatively, a similar amount of wetting liquid is placed inside second guide section 220 (FIGS. 6 and 7B). As mentioned above, in this configuration the wetting liquid does not leak through the unopened of diaphragm and is prevented from entering the first guide section 270 and sheath 200, so that the catheter is not wetted prior to use. This configuration may have the advantage of prolonging the shelf life of the device. The diaphragm may be flat or may include extension 141 (as illustrated in FIGS. 7A and 7B, respectively). Once filled, tape strip 50 or another suitable closure is placed over the aperture or outlet to retain the wetting liquid 160 within the second guide section 20 (FIG. 7B). In still another configuration, the throughbore 23 of the second guide section 20 is a narrow throughbore resembling throughbore 74 of first guide section 70, as shown in FIGS. 2B and 2D, and is capable of containing the necessary amount of wetting liquid for wetting the hydrophilic catheter. This embodiment may be preferred for ease of manufacturing. Still another alternative is to include wetting liquid in both the sheath/first guide section and in the second guide section, particularly if a larger volume of liquid is desired for wetting the catheter.

Thus assembled, an above-described catheterization device, including wetting liquid and sealing tape or other suitable closure sealing the aperture of the catheter introducer, is sterilized in accordance with standard practices for similar medical devices (e.g., conventional irradiation techniques). The device is then stored in a sterile disposable wrapper until needed. In certain embodiments, the catheter device is part of a kit that includes one or more antiseptic-soaked swabs. Optionally, the kit may also contain gloves, a specimen container and/or a urine measuring container. Preferably the urine measuring container is a bag with volumetric markings and a specimen sampling port. The container is either already affixed to the catheter and/or sheath closure, or is adapted for attaching to the urine outlet at the time of use. As mentioned above, the urine container and the catheter sheath are attached or attachable in such a way that the wetting liquid cannot mix with the urine, and such that the catheter cannot slip into the collection bag, as illustrated in FIG. 8.

When the pre-wetted catheter configuration of the device is employed, the procedure commences immediately by first cleansing the urethral area, the person performing the catheterization removes the closure from aperture 27 of second guide section 20 or 220. For instance, an adherent seal is removed by pulling on a non-adherent portion, tab 52 (shown in FIGS. 1A and 7B). Outlet 98 of catheter end 96 is positioned for discharging into either a collection or measuring container or bag, a portable waste receptacle, a toilet, or a specimen container. The catheter outlet may be conveniently attached to a collection vessel with precise measuring marks, to permit more accurate measurement of urine output than is typically possible with conventional hydrophilic catheter assemblies. Alternatively, a disposable collection vessel, which may include volumetric indicia and a specimen retrieval port is combined with the introducer/catheter/sheath unit, for convenience.

The user's hands, while preferably being clean, do not have to be strictly "sterile" or gloved for this procedure, as long as care is taken not to directly touch the area of the urethral opening or the catheter during the catheterization. It is also important that the user not disconnect the two guide sections, if the catheter introducer is separable, or to otherwise breach the seal provided by diaphragm annular ring 44 such that outside contaminants can be introduced into the sterile interior of catheter introducer 15, or wetting liquid can spill.

Referring to FIGS. 1A-B, 2A, C, 6, and 7A-B, grasping catheter introducer 15 on the outer surface 28, the body contacting collar 37 is disposed against the urethral opening such that aperture 27 of second guide section 20 or 220 is aligned axially with the urethral opening. The catheter 90 is grasped through the soft, flexible sheathing material 100 (e.g., near the sheath retaining collar 86 of first catheter guide 70 (FIGS. 4A, B and E)) and the tip end 92 of the catheter is manually advanced in the first guide section until the scored central portion 42 or 142 of diaphragm 40 or 140 has been punctured or pierced by the tip end 92 of catheter 90. As a result, a tight fitting central aperture 46 or 146 in diaphragm 40 or 140 is formed through which the tip end of the catheter protrudes into the second guide section. As previously described, diaphragm 40 or 140 preferably comprises a conformable extension 41 or 141 made of a thin elastomeric material, but it may be shaped differently, as long as it is capable of functioning similarly to initially keep the wetting liquid from contacting the hydrophilic catheter, is penetrable to form and maintain a snug fitting, fluid blocking aperture 46 or 146 around the moving catheter.

If the catheter is not initially provided in wetted condition, and the second guide section contains the wetting liquid (FIG. 7B), the foregoing procedure is modified by first piercing the diaphragm and retracting the catheter tip, and allowing the liquid to enter the first guide section and sheath, to contact the hydrophilic portion of the catheter. If the second guide section is compressible, squeezing the catheter introducer, or at least the second guide section, may be employed to help expel the liquid through the diaphragm's aperture into the first guide section and where it can flow into the sheath lumen. The device can be inverted and manipulated to ensure that the liquid contacts the entire portion of the catheter that is enclosed by the sheath and first guide section. Squeezing of the compressible catheter introducer, or the second guide section and thereby contorting a flexible diaphragm and applying fluid force on the diaphragm may also be helpful prior to, or together with piercing by the catheter tip, to open the diaphragm. After the catheter becomes thoroughly wetted (e.g., about 20-30 seconds), the procedure then continues with removing the pressure resistant seal or cover at the outlet of the catheter introducer, cleansing the urethral opening, reinserting the catheter in the diaphragm aperture, and proceeding with moving the catheter forward into the second guide section and the urethra. Preferably, little or none of the wetting liquid is carried forward or spilled through the diaphragm as the catheter emerges from the catheter introducer.

Upon moving the catheter tip through the first guide 70 and into the second guide section 20, the resulting excess length of sheath 100 or 200 is drawn up and becomes gathered 105 adjacent the first guide section (FIGS. 1B and 2C). While continuing to hold catheter introducer 15 in place against the urethral opening, the user's grasp on catheter 90 through sheath 100 or 200 is repeatedly repositioned, as necessary, for gently urging the hydrophilic catheter 90 out of the introducer and into the urethral opening, through the urethra and finally into the bladder for a sufficient distance to permit draining of accumulated urine. Referring to the embodiment shown in FIGS. 2B and 2D, tapered portion 25 and neck 26 help to guide the catheter into alignment with aperture 27. The internal diameters of throughbores 22, 74, reservoir aperture 27, diaphragm aperture 46, guide tapered inlet 75 and guide outlet 76 are slightly larger than the outer diameter of catheter 90, so that the catheter, even when thoroughly wetted and slippery, can move slightly radially and can slide longitudinally. The throughbore diameters 22, 74 are restrictive enough, however, that the catheter introducer 15 prevents a soft, flexible hydrophilic catheter from bending and provides the catheter sufficient rigidity and support to be readily inserted into the urethra. Less flexible hydrophilic catheters may be used satisfactorily with a catheter introducer similar to that shown in FIGS. 7A-B without the need for the support of a narrow throughbore.

Referring now to FIGS. 8 and 9, a urine collection bag may be attached to the catheter and may include calibrated volume markings 132 for providing an accurate urine output volume measurement, and/or the bag may include a urine sampling port 134 for withdrawing a specimen for analysis (FIG. 8). Alternatively, if a basic introducer/catheter/sheath assembly as shown in FIGS. 1A-B is employed, the user attaches the catheter's urine outlet to a suitable collection container or otherwise provides for urine disposal.

As necessary, the catheter introducer is held in place at the urethral opening and the catheter is supported through the sheath until completion of urine evacuation and removal of the catheter. The catheter is withdrawn from the urethra essentially by reversing the insertion procedure, to resume the catheter's pre-use position inside the first guide section and sheath. After withdrawal, the catheter is again held in place within the first guide section and the sheath, where it is prevented from slipping into a urine collection vessel. The unit is easily disposed of in a sanitary manner. The entire catheterization process can usually be accomplished in about 5 minutes or less.

Using the new catheter device provides for better lubrication of the catheter to reduce the discomfort or irritation typically associated with urethral catheterization. Spillage of liquids used to wet the hydrophilic catheter is avoided. This device is also an improvement over other unitized catheter assemblies in that it provides more options for the user, such as elimination of the need for a lubricant gel and disposal of waste in a conventional toilet. Exemplary embodiments also provide for accurate measurement of urine output using conventional containers without having to first open a collection bag, and collection of a specimen for analysis. It is more adaptable for use in the home or in a public restroom, and lends itself more readily for use in self-catheterization. The catheterization procedure and above-described device enable the user to easily maintain sterile technique to avoid introduction of microbial contaminants into the upper urethra and bladder. Also, the new catheterization device provides a degree of protection to medical personnel from directly contacting a catheter that may have been exposed to body fluids possibly contaminated with virus. The catheter device exemplified herein can be manufactured economically for use by hospitals, emergency care facilities, nursing homes, rehabilitation centers and the like.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A urinary catheterization device suitable for self-catheterization, the device comprising:
   a catheter introducer comprising a first guide section including an inlet for receiving a urinary catheter tip and a second guide section including an aperture for releasing said catheter tip, said second guide section comprising a cavity adapted for initially containing an amount of a wetting liquid, and, optionally, a removable aperture cover, said aperture adapted for contacting a urethral opening;
   a catheter made out of polyvinylchloride coated with polyvinylpyrrolidone comprising a tip having at least one urine inlet, a urine outlet, and an outer surface including a urethra-insertable portion, and said tip being initially disposed in said first guide section;
   a flexible walled sheath comprising first and second ends, a lumen, and a length that is less than that of said catheter, said sheath first end being sealingly attached to said catheter at a non-urethra-insertable location on said catheter adjacent to said urine outlet, and said sheath second end being sealingly attached to said first guide section, whereby said catheter tip is initially retained in said first guide section and prevented from slipping into said sheath lumen, and at least said urethra-insertable portion of said catheter being enclosed in said sheath lumen, said sheath lumen adapted for containing said liquid for wetting said enclosed portion of said hydrophilic catheter; and
   a diaphragm disposed in said catheter introducer between said first and said second guide sections, and adapted for being pierced by said catheter tip to form a leakage resistant opening for a wetted hydrophilic catheter, said diaphragm capable of preventing flow of said wetting liquid into said first guide section prior to said diaphragm being opened,
   wherein said wetting liquid is one of water or saline, wherein while oriented such that said second guide section is above said sheath lumen said wetting liquid enters said first guide section and flows into said sheath lumen and onto said urethra-insertable portion after said diaphragm is pierced and said catheter tip is retracted, and said amount of said wetting liquid is sufficient to wet said urethra-insertable portion of said catheter to render said portion of catheter lubricious within thirty seconds of exposure to said wetting liquid, said urethra-insertable portion not wetted prior to said diaphragm being pierced;
   wherein none of the wetting liquid is carried forward or spilled through the diaphragm as the catheter emerges from the catheter introducer.

2. The device of claim 1, wherein said diaphragm comprises an extension that protrudes into said second guide section and is substantially conformable to the shape of said catheter tip and to the circumference of a said wetted hydrophilic catheter.

3. The device of claim 1, wherein said first guide section comprises a cavity in fluid flow communication with said sheath lumen, and said sheath lumen and/or said first guide section contains an amount of said wetting liquid sufficient to wet said urethra-insertable portion of said catheter to render said portion lubricious.

4. The device of claim 1, wherein said second guide section is resiliently compressible.

5. The device of claim 1, wherein said flexible walled sheath is impermeable to said wetting liquid.

6. The device of claim 5, wherein said sheath interior comprises a grip enhancing surface.

7. The device of claim 1, further comprising a urine collection container attached to a said catheter and adapted for receiving said catheter urine outlet, wherein said sheath lumen is not in fluid communication with said container and said wetting liquid is prevented from entering said container.

8. The device of claim 1, wherein said second guide section comprises a body-contacting collar and a frustoconical segment having its smallest outer diameter adjoining said collar.

9. The device of claim 1, wherein said catheter introducer further comprises a removable closure on said aperture.

10. The device of claim 1, wherein said sheath is of approximately equal length to that of said urethra-insertable catheter portion and said catheter tip is retained in said first guide section and is prevented from slipping into said sheath interior when said device is fully extended.

11. The device of claim 1, wherein said first and second guide sections are releasably joined together such that said diaphragm is removable.

12. The device of claim 1, wherein said first guide section and said second guide section are fixedly joined together with said diaphragm disposed therebetween.

13. The device of claim 1, wherein said diaphragm comprises a leak-resistant extension.

14. A kit for catheterizing a urinary bladder comprising:
   a catheterization device according to claim 1;
   a disposable package enclosing said catheterization device; and
   at least one antiseptic swab.

15. The kit of claim 14 further comprising a urine collection container having volumetric indicia.

16. A method of deterring or preventing spillage of a wetting liquid for a hydrophilic catheter during catheterization of a urinary bladder, the method comprising:
   (a) providing the device of claim 3, 7, or 14, providing for urine disposal or collection, if necessary, and removing any cover from said introducer;
   (b) placing the catheter introducer adjacent to the urethral opening of an individual in need of catheterization;
   (c) grasping said flexible walled sheath and wetted hydrophilic catheter together at one or more first position or series of positions along the urethra-insertable length of said catheter, and urging the catheter tip into the diaphragm such that said diaphragm is pierced and such that a portion of said sheath is caused to collapse toward said first guide section;
   (d) regrasping said flexible walled sheath and wetted catheter together at one or more second position or series of positions along the urethra-insertable length of said catheter, and moving the catheter through said pierced diaphragm, whereby a further portion of said sheath is caused to collapse toward said first guide section and said pierced diaphragm or a portion thereof forms a leak resistant circumferential seal around said moving catheter;
   (e) regrasping said flexible walled sheath and wetted catheter together at one or more third position or series of positions along the urethra-insertable length of said catheter, and urging the catheter tip through said second guide section and aperture, if present, and into the urethra to the urinary bladder, whereby further portions of said sheath are caused to collapse toward said first guide and urine flows into said catheter tip and out said urine outlet; and (f) after emptying the bladder, removing the catheter from the bladder and urethra by substantially reversing each of steps (e)-(b).

17. The method of claim 16 further comprising (g) measuring the amount of urine collected in said container.

18. A method of deterring or preventing spillage of a wetting liquid during catheterization of a urinary bladder, the method comprising:

(a) providing the device of claim 4 wherein said device comprises a removable seal covering said aperture of said catheter introducer and said second guide section contains at least an amount of a wetting liquid sufficient to wet said insertable portion of said catheter to render said portion lubricious;

(b) providing for urine disposal or collection;

(c) grasping said flexible walled sheath and said catheter together at one or more first position or series of positions along the urethra-insertable length of said catheter, and urging the catheter tip into the diaphragm such that said diaphragm is pierced and in so doing causing a portion of said sheath to collapse toward said first guide section;

(d) withdrawing said catheter tip from said pierced diaphragm leaving an opening between said first and second guide sections which allows said wetting liquid to enter said first guide section;

(e) optionally, compressing at least said second guide section of said catheter introducer to facilitate movement of said liquid through said diaphragm opening and into said first guide section and sheath interior;

(f) after said catheter is wetted by said liquid in said sheath and first guide section, removing said seal and placing said aperture against the urethral opening of an individual in need of catheterization;

(g) returning said wetted catheter tip through said diaphragm opening to form a leakage resistant circumferential seal around the moving catheter;

(h) regrasping said flexible walled sheath and wetted catheter together at one or more subsequent position or series of subsequent positions along the sheath-enclosed urethra-insertable length of said catheter, and urging the catheter tip through said second guide section, through said aperture, into the urethra and into the urinary bladder, whereby further portions of said sheath are caused to collapse toward said first guide, until urine flows into said catheter tip and out said urine outlet;

(i) after emptying the bladder, removing the catheter from the bladder and urethra by reversing step (h).

\* \* \* \* \*